United States Patent

Inukai et al.

[11] Patent Number: 5,865,761
[45] Date of Patent: Feb. 2, 1999

[54] APPARATUS FOR DETECTING BLOOD PRESSURE AND ELECTROCARDIOGRAPHIC WAVEFORMS

[75] Inventors: Hidekatsu Inukai, Nagoya; Hiroshi Sakai, deceased, late of Komaki, both of Japan, by Hiroko Sakai, legal heir

[73] Assignee: Colin Corporation, Komaki, Japan

[21] Appl. No.: 851,495

[22] Filed: May 5, 1997

[51] Int. Cl.⁶ .................................................. A61B 5/0205
[52] U.S. Cl. .......................................................... 600/513
[58] Field of Search ..................................... 600/513, 499, 600/490, 492, 493, 494, 485

[56] References Cited

U.S. PATENT DOCUMENTS 4,722,354  2/1988  Axelgaard et al. ..................... 607/152
4,726,382  2/1988  Boehmer et al. .

FOREIGN PATENT DOCUMENTS 0 251 273-A1  1/1988  European Pat. Off. .
0 553 372-A1  8/1993  European Pat. Off. .
42 17 388-A1  12/1993  Germany .

*Primary Examiner*—Scott M. Getzow
*Attorney, Agent, or Firm*—Oliff & Berridge, PLC

[57] ABSTRACT

An apparatus that detects both the blood pressure and the electrocardiographic waveform of a living subject and that can be quickly and easily fitted to the living subject includes a cuff that is wrapped around a portion of the living subject for detecting the subject's blood pressure, and a flexible electrocardio electrode on the inner surface of the cuff for detecting the electrocardiographic waveform generated by the living subject's cardiac muscle. When the cuff is wrapped around a portion of the living subject, the electrocardiographic electrode is automatically fitted and correctly positioned on the living subject. Because the electrocardio electrode does not have to be separately fitted and attached to the living subject, the "set up" time is significantly reduced. Thus, the apparatus of this invention is especially useful in emergency medical situations, where rapid measurements are required.

25 Claims, 6 Drawing Sheets

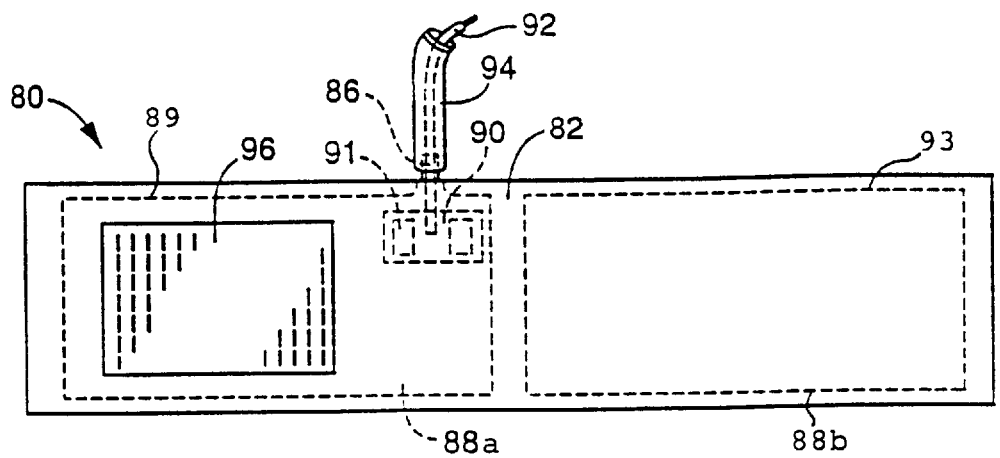
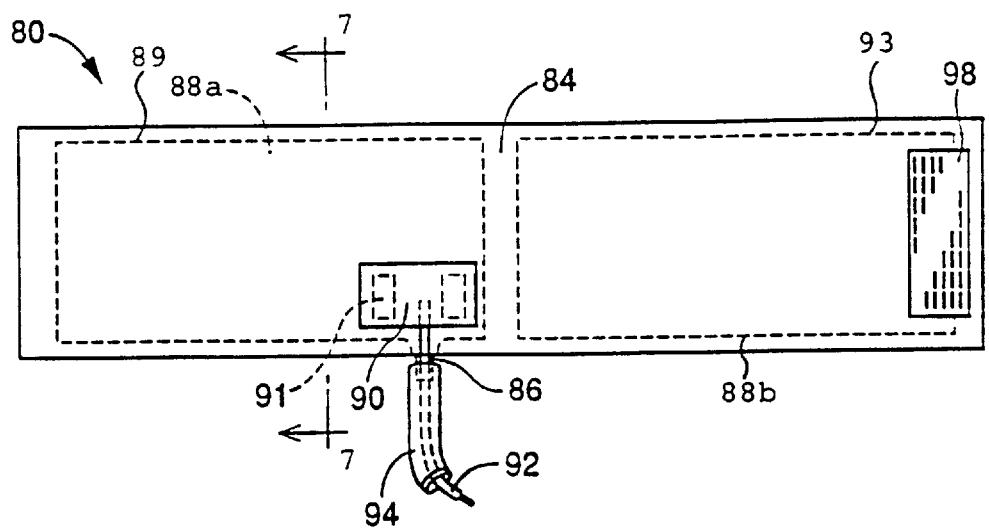

APPARATUS FOR DETECTING BLOOD PRESSURE AND ELECTROCARDIOGRAPHIC WAVEFORMS

BACKGROUND OF THE INVENTION

1. Field of the Invention

This invention relates to blood pressure measuring devices. More specifically, this invention is directed to an apparatus for detecting both the blood pressure and electrocardiographic waveform of a living subject.

2. Description of Related Art

The blood pressure of a living subject is typically measured with the use of a cuff that is wrapped around a portion of the living subject. The cuff applies pressure to the living subject and the living subject's blood pressure is measured using a well known oscillometric method, which is based on detecting changes in the amplitude of a synchronous wave pulsation as the pressure applied by the cuff is gradually released.

In certain medical situations, it is desirable to obtain both the blood pressure and an electrocardiogram of the living subject. In order to obtain an electrocardiogram, the electrocardiographic waveform, generated as a result of the action potential of the subject's cardiac muscle, must be detected. The electrocardiographic waveform is typically detected with electrocardio electrodes that are attached to the living subject.

In order to detect both the electrocardiographic waveform and the blood pressure of the living subject, the cuff for measuring the blood pressure and the electrocardio electrodes for measuring the electrocardiographic waveform must be separately fitted and attached to the living subject. The additional time required to separately attach and fit the cuff and electrocardio electrodes to the living subject may be detrimental to the living subject in situations where a rapid measurement is required, e.g., an emergency medical situation.

SUMMARY OF THE INVENTION

This invention provides an apparatus that detects both the blood pressure and the electrocardiographic waveform of a living subject and that can be quickly and easily fitted to the living subject. The apparatus comprises a cuff that is wrapped around a portion of the living subject for detecting the subject's blood pressure, and a flexible electrocardio electrode on the inner surface of the cuff for detecting the electrocardiographic waveform generated by the living subject's cardiac muscle.

The apparatus of this invention is attached to the living subject by wrapping the cuff around a portion of the living subject. When the cuff is wrapped around a portion of the living subject, the electrocardiographic electrode is automatically fitted and correctly positioned on the living subject. Thus, the living subject's blood pressure and electrocardiographic waveform can be detected simultaneously. Because the electrocardio electrode does not have to be separately fitted and attached to the living subject, the "set up" time is significantly reduced. Thus, the apparatus of this invention is especially useful in emergency medical situations, where rapid measurements are required.

In a preferred embodiment, the electrocardio electrode comprises electrically conductive fabric that makes up at least a portion of the inner surface of the cuff. Thus, the electrocardio electrode is integrated into at least a portion of the fabric that makes up the cuff. This ensures that the electrocardio electrode does not interfere with the blood pressure measurement.

In another embodiment, the electrocardio electrode comprises a separate piece of conductive fabric that is attached to the inner surface of the cuff with a quick-release attachment mechanism. Thus, the electrocardio electrode can be easily removed and replaced if it becomes inoperative.

These and other features and advantages of this invention are described in or are apparent from the following detailed description of the preferred embodiments.

BRIEF DESCRIPTION OF THE DRAWINGS

The preferred embodiments of this invention will be described in detail, with reference to the following figures, wherein:

FIGS. 5 and 6 are plan views of a second preferred embodiment of the blood pressure/electrocardiographic waveform detecting apparatus of this invention;

DETAILED DESCRIPTION OF PREFERRED EMBODIMENTS

Figure 1:
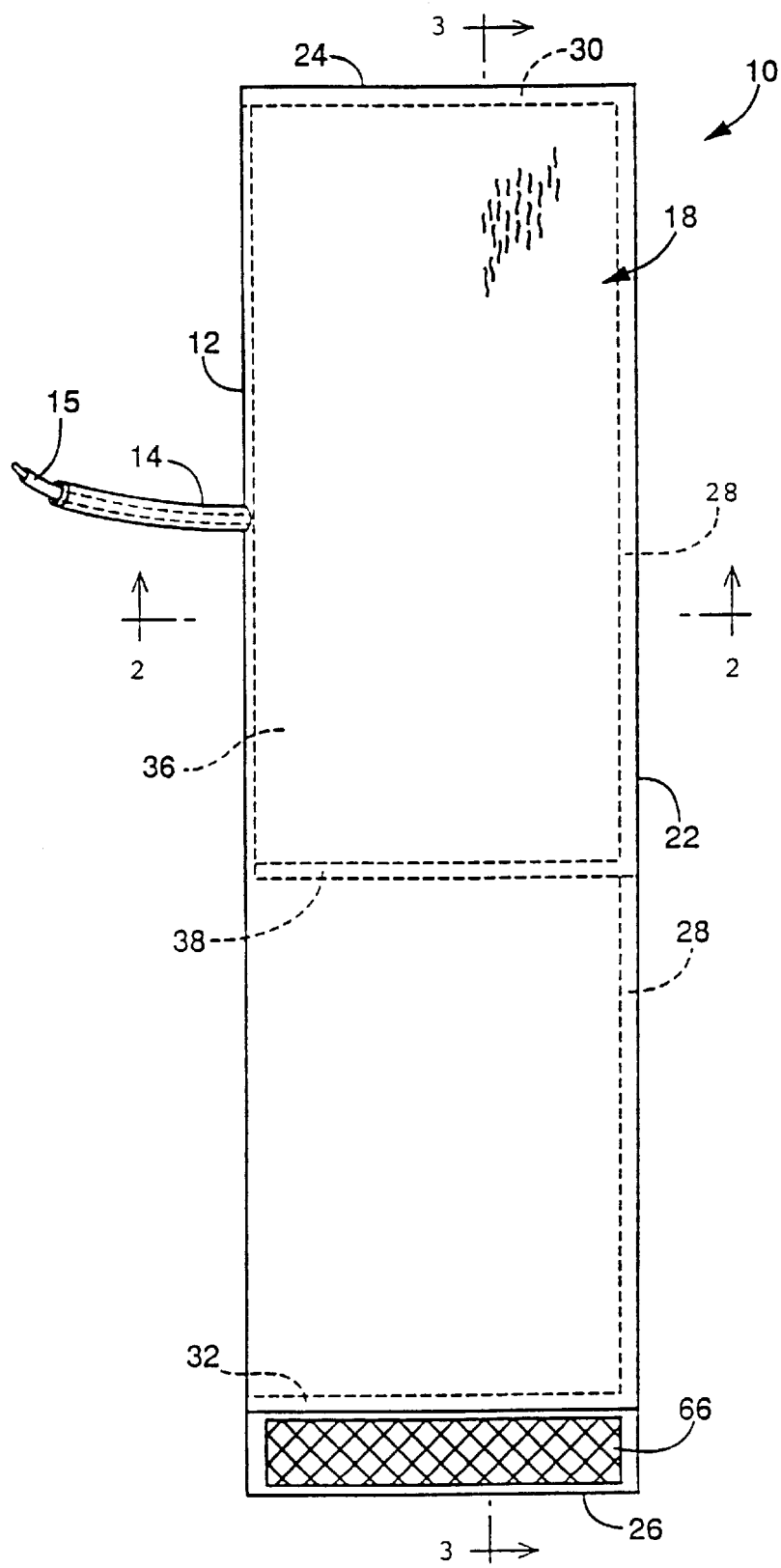
FIG. 1 is a plan view of a first preferred embodiment of the blood pressure/electrocardiographic waveform detecting apparatus of this invention.
Figure 2:
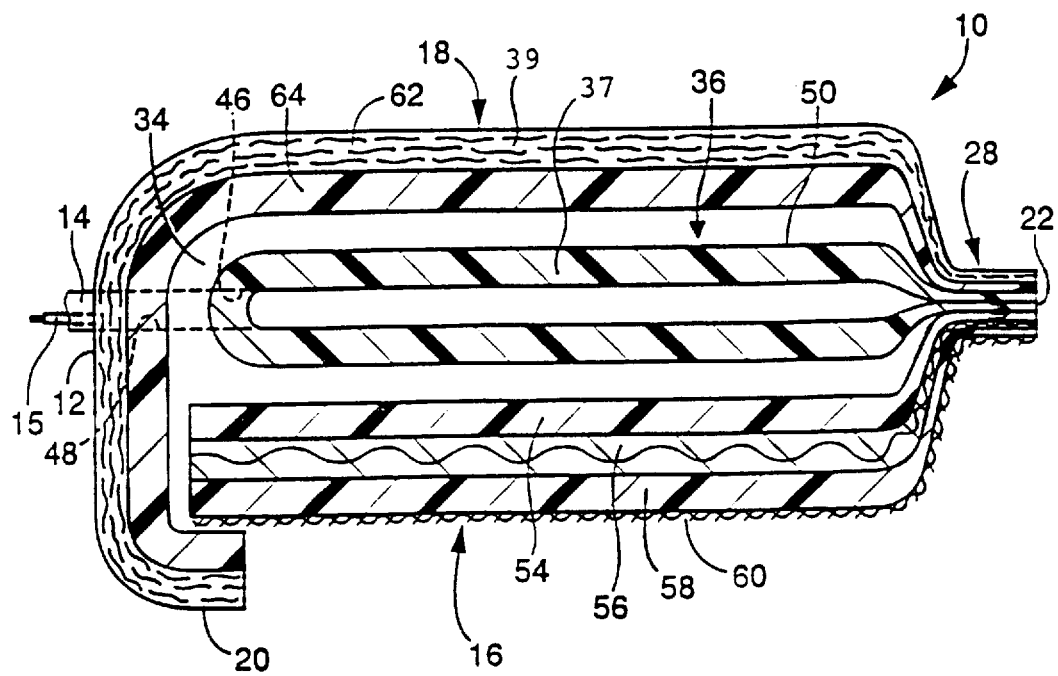
FIG. 2 is a sectional view of the embodiment of FIG. 1 taken along the section line 2—2 of FIG. 1.
Figure 3:
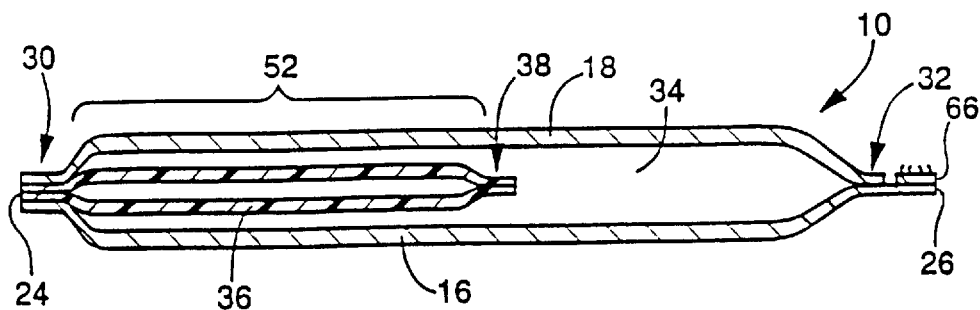
FIG. 3 is a sectional view of the embodiment of FIG. 1 taken along the section line 3—3 of FIG. 1.

FIGS. 1–3 illustrate a first preferred embodiment of the blood pressure/electrocardiographic measuring apparatus of this invention. The apparatus comprises a cuff that is preferably approximately 50 centimeters long, approximately 14 centimeters wide, and approximately 1.5 millimeters thick. A flexible inflation tube 14, which is preferably made from rubber or similar material, is mounted on one of the long sides 12 of the cuff 10.

A flexible lead wire 15 is disposed inside the inflation tube 14. As shown in FIGS. 2 and 3, the cuff 10 comprises an outer member 16 and an inner member 18. The inner member 18 is folded to form the long side 12 of the cuff 10, and is attached to the outer member 16 at the folded portion 20, preferably with an adhesive, as shown in FIG. 2.

The inner member 18 and the outer member 16 are preferably welded together on the other long side 22 and on the short sides 24 and 26. Thermal compression bonding is preferably used to weld the inner member 18 and the outer member 16 at the seal areas 28, 30 and 32.

By sealing the inner member 18 and the outer member 16 in this way, a bag-shaped cuff 10 is formed with an inner space 34. An inflatable expansion bag 36 is disposed inside the inner space 34. The inflatable expansion bag 36 is preferably shorter than the outer member 16 and the inner member 18. The width of the inflatable expansion bag 36 is preferably substantially the same as the width of outer member 16.

The inflatable expansion bag 36 is preferably formed by a film 37 that has a high tensile strength and a high tensile elasticity. The film 37 is suitably a 0.2 millimeter thick film of ethylene vinyl acetate resin with a composition of 15–20% vinyl acetate and 80–85% linear low-density polyethylene. The film 37 is folded along its long side and sealed, preferably by thermal compression bonding, at the seal areas 28 and 30 together with the outer member 16 and the inner member 18, and at the seal area 38.

The inflation tube 14 is preferably attached to the inflatable expansion bag 36 by thermal compression bonding. One end of the inflation tube 14 preferably extends through hole 46 formed at the folded portion of the film 37. The other end of the inflation tube 14 extends through a hole 48 which is formed on the long side 12 of the inner member 18.

The inflatable expansion bag 36 expands when air is introduced into it through the inflation tube 14. When the inflatable expansion bag 36 expands, it presses against the inner member 18 and the outer member 16 along a contact area 52. This in turn causes the cuff 10 to expand along the contact area 52.

The outer member 16 preferably comprises four tightly adhered layers 54, 56, 58 and 60. The first layer 54 is suitably polyethylene resin with a thickness of approximately 0.04 millimeters. The second layer 56 is suitably a cloth woven with a medium-low pressure polyethylene fiber at a weaving density of 10×10 per inch. The third layer 58 is suitably a polyethylene resin layer with a thickness of approximately 0.04 millimeters. The fourth layer 60, which is the outer layer, is preferably a nylon pile comprised of wave-shaped nylon fibers that extend along a longitudinal direction and loop-shaped nylon fibers that protrude to one side of the wave-shaped fibers. The nylon pile has a density of 65 g/m$^2$ and is obtained by a 40/20 thread use, i.e., a Velcro™-type layer. The first layer 54 and the second layer 56 contribute to the tensile strength of the outer member 16 so that the outer member 16 is not damaged when pressure is applied to it by the inflatable expansion bag 36.

The inner member 18 preferably comprises two tightly adhered layers 62 and 64. At least a portion of the outer layer 62 is electrically conductive. In the embodiment of FIGS. 1–3, the entire outer layer 62 is electrically conductive and formed from a non-woven electrically conductive fabric with a thickness of approximately 0.55 millimeters. The layer 62 is suitably a blended yarn composed of 35% rayon, 35% polyester and 30% carbon fiber with a density of 60 g/m$^2$. The lining layer 64 is preferably a polyethylene resin with a thickness of approximately 0.05 millimeters.

The lead wire 15 is connected to the electrically conductive outer layer 62 of the inner member 18 through a small opening (not shown) in the inflation tube 14, preferably with a conductive adhesive. A fastener pad 66 is attached to the cuff 10 at the short side 26. The fastener pad 66 is preferably a Velcro™-type fastener comprising a plurality of hook-shaped components. The hook-shaped components engage the wave-shaped nylon fibers on the outer layer 60 of the outer member 16 when the cuff 10 is wrapped around a portion of a living subject.

Figure 4:
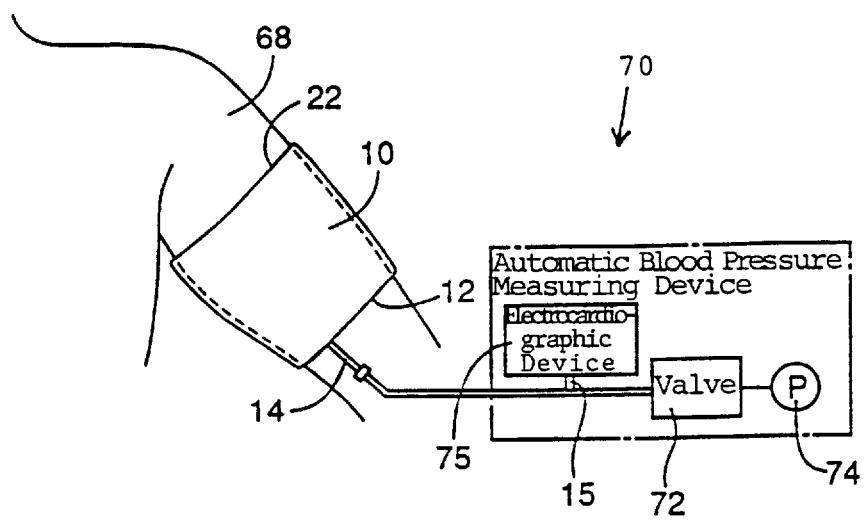
FIG. 4 is a schematic diagram of a blood pressure/electrocardiographic waveform measuring system that incorporates the first preferred embodiment of the blood pressure/electrocardiographic waveform detecting apparatus of this invention.

FIG. 4 shows a blood pressure/electrocardiographic waveform measuring system 70 that incorporates the first preferred embodiment of the blood pressure/electrocardiographic waveform detecting apparatus of this invention.

The cuff 10 is attached to a portion of a living subject, such as the upper portion of an arm 68. The cuff 10 is preferably positioned on the upper arm 68 so that the long side 22 is closest to the shoulder, and the long side 12 is closest to the elbow. The cuff 10 is wrapped around the upper arm 68 so the inner member 18 contacts the upper arm 68. As explained above, the hook-shaped components on the fastener pad 66 engage the wave-shaped fibers on the layer 60 of the outer member 16. Thus, the cuff 10 is held in place on the upper arm 68.

To take a measurement, the inflation tube 14 is connected to a pump 74 through a compressed air inflation valve 72. The lead wire 15 is connected to an electrocardiographic device 75.

The cuff 10, the compressed air inflation valve 72, the pump 74 and the electrocardiographic device 75 together comprise an automatic blood pressure measurement system 70.

The process of measuring the blood pressure of a living subject with the automatic blood pressure measurement system 70 is well known in the art. Accordingly, details of this process will not be described. Generally, the automatic blood pressure measurement system 70 controls the blood pressure measurement by controlling the amount of air inserted and released from the inflatable expansion bag 36 via the inflation tube 14.

A signal corresponding to the electrocardiographic waveform of the living subject is detected by the electrically conductive layer 62 of the inner member 18. The signal is input to the electrocardiographic device 75 via the lead wire 15. The electrocardiographic device 75 determines the electrocardiographic waveform based on the signal detected by the layer 62 and a signal detected by another electrocardio electrode that is in contact with another portion of the living subject (not shown).

The blood pressure/electrocardiographic waveform detection apparatus of this invention detects the blood pressure and electrocardiographic waveform of a living subject simultaneously. Accordingly, the measurement time is significantly reduced. In addition, the detection of the electrocardiographic waveform does not interfere with the detection of the blood pressure of the living subject. Furthermore, because the cuff 10 of this invention is preferably composed of nylon pile, non-woven fabric, polyethylene and ethylene vinyl acetate resin, the cuff 10 may be destroyed via incineration without releasing any harmful gases. Accordingly, the cuff 10 can be used as a disposable cuff in situations where it is desirable to dispose of the cuff 10 after it has been used on a patient.

Figure 7:
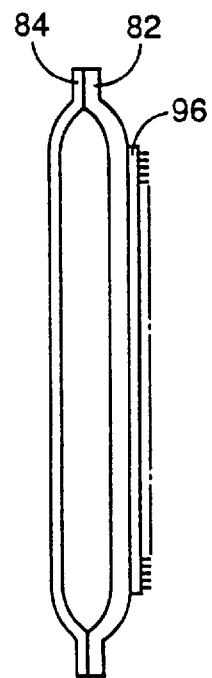
FIG. 7 is a sectional view of the embodiment of FIGS. 5 and 6 taken along the section line 7—7 of FIG. 6.

FIGS. 5–7 illustrate a second preferred embodiment of the blood pressure/electrocardiographic waveform detection apparatus of this invention. In the second preferred embodiment, the cuff 80 comprises an outer member 82 and an inner member 84. The outer member 82 and the inner member 84 preferably have substantially the same shape, and are preferably joined together along an outer area indicated by the dashed lines 89 and 93. The outer member 82 and the inner member 84 are preferably made of a synthetic resin material, suitably a material made of soft vinyl chloride or nylon, and are preferably joined with an adhesive or by high frequency welding.

When the outer member 82 and the inner member 84 are joined along the area indicated by dashed lines 89 and 93, airtight bag portions 88a and 88b are created. In the preferred embodiment, only the airtight bag portion 88a is used to apply pressure to the living subject.

At the time the outer member 82 and the inner member 84 are joined, a connection cylinder 86 is preferably positioned between the outer member 82 and the inner member 84. The connection cylinder 86 partially extend into and out of the airtight bag portion 88a.

A flexible electrically conductive fabric 90, preferably a non-woven fabric, is attached to the inner member 84 within the boundary of the airtight bag portion 88a. The electrically conductive fabric 90 is suitably a blended yarn formed from 35% rayon, 35% polyester and 30% carbon fiber, and is preferably approximately 0.55 millimeters thick with a density of 60 g/m².

The electrically conductive fabric 90 is preferably attached to the inner member 84 with a quick-release mechanism, suitably a double-sided adhesive tape 91. The electrically conductive fabric 90 is preferably attached in close proximity to the connection cylinder 86. An inflation tube 94 is attached to connection cylinder 86. A lead wire 92 is disposed inside the inflation tube 94. One end of the lead wire 92 is disposed between the conductive fabric 90 and the inner member 84 to electrically contact the electrically conductive fabric 90.

A pair of fasteners 96 and 98 are attached to the outer member 82 and the inner member 84, respectively. The fasteners 96 and 98 are preferably sewed onto the cuff 80. The fasteners 96 and 98 are preferably Velcro™-type fasteners, with one of the fasteners comprising a plurality of hooks made of synthetic resin and the other fastener comprising a plurality of loop-shaped fibers that engage the plurality of hooks when the fasteners 96 and 98 are brought into physical contact. The fasteners 96 and 98 are positioned to come into physical contact when the cuff 80 is wrapped around a portion of a living subject.

Figure 8:
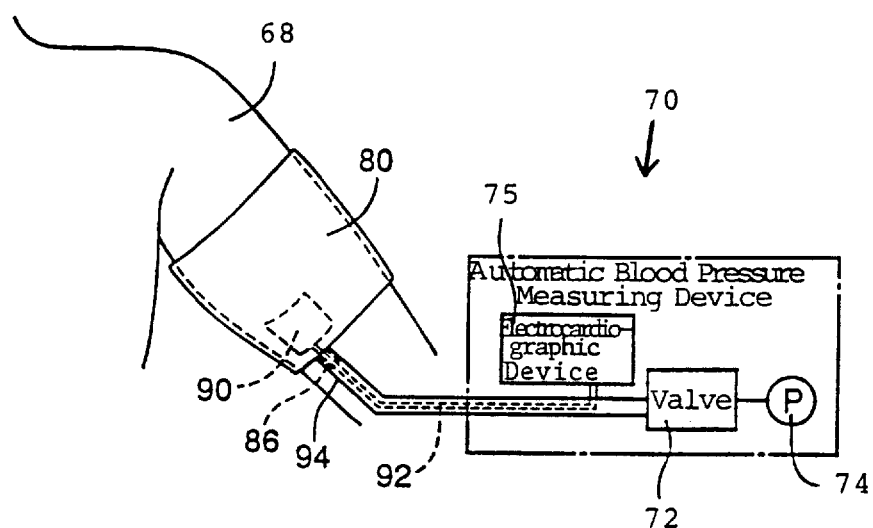
FIG. 8 is a schematic diagram of a blood pressure/electrocardiographic waveform measuring system that incorporates the second preferred embodiment of the blood pressure/electrocardiographic waveform detecting apparatus of this invention.

FIG. 8 shows a blood pressure/electrocardiographic waveform measuring system 70 that incorporates the second preferred embodiment of the blood pressure/electrocardiographic waveform detecting apparatus of this invention. The cuff 80 is wrapped around the upper arm 68 and is held in place by bringing the two fasteners 96 and 98 into physical contact. The cuff 80 is attached so that the connection cylinder 86 is closest to the elbow.

The inflation tube 94, which extends from the connection cylinder 86, is connected to the air pump 74 through the compressed air inflation valve 72. The lead wire 92 is connected to the electrocardiographic device 75.

In the embodiment of FIGS. 5–8, the conductive fabric 90 functions as the electrocardio electrode for detecting the electrocardiographic waveform. Because the conductive fabric 90 is attached with a quick-release mechanism, it can be easily removed and exchanged if it becomes inoperative.

While this invention has been described in conjunction with the specific embodiments outlined above, it is evident that many alternatives, modifications and variations will be apparent to those skilled in the art. For example, in the embodiment of FIGS. 1–4, the surface 50 of the inflatable expansion bag 36 can be attached to either the outer member 16 or the inner member 18. Alternatively, the surface 50 of the inflatable expansion bag 36 can be attached to both the outer member 16 and the inner member 18.

In addition, the material used for the inner member 16 and the outer member 18 does not have to be a material capable of expanding and contracting. The entire layer 62 is shown and described as an electrically conductive layer in the embodiment of FIGS. 1–4. However, a layer 62 can be used in which only a portion is electrically conductive. In this case, the electrically conductive portion must contact the living subject when the cuff is attached to the living subject. Additionally, the lead wire 15 must electrically contact the electrically conductive portion of the layer 62.

In the embodiment of FIGS. 5–8, the outer member 82 and the inner member 84 are attached together along substantially their entire perimeters. However, the outer member 82 and the inner member 84 may be only partially attached together. For example, the outer member 82 and the inner member 84 may be attached together only along the area that corresponds to the bag portion 88a, i.e., the area indicated by dashed line 89.

Furthermore, in the two embodiments described above, the lead wires 15 and 92 are disposed inside the inflation tubes 14 and 94, respectively. However, other means of guiding the lead wire from the cuff may be utilized. For example, the lead wires 15 and 92 may be wrapped around the inflation tubes 14 and 94, respectively.

Accordingly, the preferred embodiments of the invention as set forth above are intended to be illustrative not limiting. Various changes may be made without departing from the spirit and scope of the invention as defined in the following claims.

What is claimed is:

1. An apparatus for detecting a blood pressure and an electrocardiographic waveform of a living subject, comprising:
   a cuff wrapable around a portion of the living subject and having an inner surface and an outer surface, the inner surface making physical contact with the living subject when the cuff is wrapped around the portion of the living subject; and
   an electrode which forms at least a portion of the inner surface of the cuff and is capable of detecting the electrocardiographic waveform of the living subject, wherein the electrode portion of the inner surface of the cuff comprises electrically conductive fabric.

2. The apparatus of claim 1, wherein the electrically conductive fabric comprises a non-woven fabric.

3. The apparatus of claim 1, wherein the electrically conductive fabric comprises 35% rayon, 35% polyester and 30% carbon fiber.

4. The apparatus of claim 1, wherein the electrode comprises the electrically conductive fabric that is attached to the inner surface of the cuff with a quick release mechanism and thereby forms said portion of the inner surface.

5. The apparatus of claim 4, wherein the quick release mechanism comprises a double-sided adhesive tape.

6. The apparatus of claim 4, wherein the electrically conductive fabric comprises a non-woven fabric.

7. The apparatus of claim 4, wherein the electrically conductive fabric comprises 35% rayon, 35% polyester and 30% carbon fiber.

8. The apparatus of claim 1, wherein the cuff comprises:
   an inner member;
   an outer member; and
   an inflatable expansion bag disposed between the inner member and the outer member.

9. The apparatus of claim 8, further comprising:
   a flexible inflation tube connected to the inflatable expansion bag; and
   a wire disposed inside the flexible inflation tube and connected to the electrode.

10. The apparatus of claim 8, wherein the electrode comprises the electrically conductive fabric that forms at least a portion of the inner member of the cuff and thereby forms said portion of the inner surface of the cuff.

11. The apparatus of claim 1, wherein the cuff comprises:

an inner member; and an outer member attached to the inner member to form an inflatable airtight bag portion between the inner member and the outer member.

12. The apparatus of claim 11, further comprising:

a connection cylinder positioned between the inner member and the outer member, the connection cylinder partially extending into and out of the airtight bag portion;

a flexible inflation tube connected to the connection cylinder; and a wire disposed inside the flexible inflation tube and capable of electrically contacting the electrode.

13. A blood pressure/electrocardiographic waveform measuring system, comprising:

a cuff wrapable around a portion of the living subject and having an inner surface and an outer surface, the inner surface making physical contact with the living subject when the cuff is wrapped around the portion of the living subject;

an electrode which forms at least a portion of the inner surface of the cuff and is capable of detecting an electrocardiographic waveform of the living subject, wherein the electrode portion of the inner surface of the cuff comprises electrically conductive fabric;

an air pump connected to an inflatable portion of the cuff; and an electrocardiographic device connected to the electrode, the electrocardiographic device capable of processing the electrocardiographic waveform detected by the electrode.

14. The system of claim 13, further comprising a flexible inflation tube that connects the air pump to the inflatable portion of the cuff.

15. The system of claim 13, further comprising a wire that connects the electrode to the electrocardiographic device.

16. The apparatus of claim 13, wherein the electrically conductive fabric comprises a non-woven fabric.

17. The apparatus of claim 13, wherein the electrically conductive fabric comprises 35% rayon, 35% polyester and 30% carbon fiber.

18. The apparatus of claim 13, wherein the electrode comprises the electrically conductive fabric that is attached to the inner surface of the cuff with a quick release mechanism and thereby forms said portion of the inner surface.

19. The apparatus of claim 18, wherein the quick release mechanism comprises a double-sided adhesive tape.

20. The apparatus of claim 18, wherein the electrically conductive fabric comprises a non-woven fabric.

21. The apparatus of claim 18, wherein the electrically conductive fabric comprises 35% rayon, 35% polyester and 30% carbon fiber.

22. The apparatus of claim 13, wherein the cuff comprises:

an inner member;

an outer member; and an inflatable expansion bag between the inner member and the outer member.

23. The apparatus of claim 22, wherein the electrode comprises the electrically conductive fabric that forms at least a portion of the inner member of the cuff and thereby forms said portion of the inner surface of the cuff.

24. The apparatus of claim 13, wherein the cuff comprises:

an inner member; and an outer member attached to the inner member to form an inflatable airtight bag portion between the inner member and the outer member.

25. The apparatus of claim 24, further comprising:

a connection cylinder positioned between the inner member and the outer member, the connection cylinder partially extending into and out of the airtight bag portion;

a flexible inflation tube connected to the connection cylinder; and a wire disposed inside the flexible inflation tube and capable of electrically contacting the electrode.

* * * * *